United States Patent
Merlen et al.

[11] Patent Number: 5,929,296
[45] Date of Patent: Jul. 27, 1999

[54] CATALYST BASED ON DEALUMINATED MORDENITE AND ITS USE FOR DISMUTATION AND/OR TRANSALKYLATION OF AROMATIC HYDROCARBONS

[75] Inventors: Elisabeth Merlen, Rueil Malmaison; Fabio Alario, Neuilly Sur Seine, both of France

[73] Assignee: Institut Francais du Petrole, France

[21] Appl. No.: 09/056,742

[22] Filed: Apr. 8, 1998

[30] Foreign Application Priority Data

Apr. 9, 1997 [FR] France ................... 97/04452

[51] Int. Cl.[6] ................ C07C 5/22; B01J 29/18
[52] U.S. Cl. ................ 585/475; 502/64; 502/78
[58] Field of Search ............... 502/78, 64; 585/475

[56] References Cited

U.S. PATENT DOCUMENTS

| | | | |
|---|---|---|---|
| 3,720,726 | 3/1973 | Mitsche et al. | 260/672 T |
| 3,723,552 | 3/1973 | Mitsche et al. | 260/668 A |
| 3,780,121 | 12/1973 | Suggitt et al. | 260/672 T |
| 3,915,895 | 10/1975 | Suggitt et al. | 252/455 Z |
| 4,150,061 | 4/1979 | Feinstein et al. | 260/672 T |
| 4,501,656 | 2/1985 | Dufresne et al. | 208/111 |
| 4,789,655 | 12/1988 | Travers et al. | 502/66 |
| 4,977,121 | 12/1990 | Dufresne et al. | 502/66 |

*Primary Examiner*—Michael Lewis
*Assistant Examiner*—Thomas G. Dunn, Jr.
*Attorney, Agent, or Firm*—Millen, White, Zelano, & Branigan, P.C.

[57] ABSTRACT

A catalyst for transforming aromatic hydrocarbons, preferably for dismutation of toluene to produce benzene and xylenes and transalkylation of toluene and aromatic compounds containing at least 9 carbon atoms per molecule, preferably trimethylbenzenes, to produce xylenes, contains a mordenite in its acid form in a proportion of 40% to 90% by weight and a binder, which is preferably alumina, and which is generally present in a proportion of 10% to 60% by weight. The mordenite contains less than 0.1% by weight of sodium and has a $SiO_2/Al_2O_3$ molar ratio of over 40–60.

10 Claims, No Drawings

CATALYST BASED ON DEALUMINATED MORDENITE AND ITS USE FOR DISMUTATION AND/OR TRANSALKYLATION OF AROMATIC HYDROCARBONS

FIELD OF THE INVENTION

The present invention relates to a catalyst for transforming aromatic hydrocarbons. More precisely, it relates to a catalyst for dismutation of toluene to produce benzene and xylenes, and transalkylation of alkylaromatic hydrocarbons, preferably transalkylation of toluene and aromatic compounds containing at least 9 carbon atoms per molecule, preferably trimethylbenzenes, to produce xylenes. The catalyst of the present invention contains a mordenite with a high silicon content and in a large proportion with respect to a binder. At least part of this mordenite is present in its acid form, generally in a proportion of 40% to 90% by weight, preferably 75% to 85% by weight, and the binder, preferably alumina, is generally present in a proportion of 10% to 60% by weight, preferably 15% to 25% by weight. The mordenite contains less than 0.1% by weight, preferably less then 0.05% by weight, of sodium, and has an $SiO_2/Al_2O_3$ molar ratio of over 70, preferably in the range 80 to 120. The present invention also concerns the use of the catalyst for dismutation and/or transalkylation of alkylaromatic hydrocarbons.

BACKGROUND OF THE INVENTION

A number of dismutation and transalkylation catalysts have already been described in the prior art. Some are based on mordenite, in particular so-called "large pore" mordenites. In United States patent U.S. Pat. No. 3,506,731, the mordenite is in its hydrogen form. This is also the case in U.S. Pat. No. 4,151,120, U.S. Pat. No. 4,1180,693 and U.S. Pat. No. 4,210,770 where the catalyst comprises mordenite in a $SiO_2/Al_2O_3$ ratio which is in the range 10 to 100 and at least one metal selected from the group formed by Ni, Co, Ag and Pd. More recently, U.S. Pat. No. 4,665,258 describes a process for dismutation of a feed containing toluene using a catalyst containing mordenite in an $SiO_2/Al_2O_3$ molar ratio of more than 30, preferably between 40 and 60, more preferably about 48.

SUMMARY OF THE INVENTION

We have discovered that, surprisingly, a catalyst for transforming aromatic hydrocarbons containing a mordenite zeolite with a $SiO_2/Al_2O_3$ molar ratio of over 70, preferably in the range 80 to 120, leads to substantially improved performances, principally in terms of toluene conversion and stability over time, over the catalysts described in U.S. Pat. No. 4,665,258, for the dismutation of toluene to produce benzene and xylenes, and for the transalkylation of toluene with alkylaromatic compounds containing at least 9 carbon atoms per molecule [AC9(+)] to produce xylenes from toluene-AC9(+) mixtures generally containing at most 50 mole % of AC9(+).

The present invention concerns a catalyst for dismutation and/or transalkylation of toluene and/or alkylaromatic compounds containing at least 9 carbon atoms per molecule which contains:

40% to 90% by weight, preferably 75% to 85% by weight, of at least one zeolite with a mordenite structure which is at least partially in its acid form, characterized in that its Si/Al molar ratio is over 35, preferably in the range 40 to 60, said mordenite containing at most 0.1% by weight (expressed with respect to zeolite) of sodium, preferably at most 0.05% by weight of sodium;

10% to 60% by weight, preferably 15% to 25% by weight, of at least one binder, preferably alumina.

The present invention also concerns a process for dismutation and/or transalkylation of toluene and/or alkylaromatic compounds containing at least 9 carbon atoms per molecule, preferably for dismutation of toluene to produce benzene and xylenes and/or transalkylation of toluene with AC9(+) compounds to produce xylenes from toluene-AC9(+) mixtures generally containing at most 50 mole % of AC9(+), said process being characterized in that the catalyst of the invention is used.

Any zeolite with a mordenite structure which is known to the skilled person is suitable for the present invention. Thus, for example, the zeolite used as a base to prepare the catalyst of the present invention is "large pore" mordenite in its sodium form, or "small pore" mordenite in its sodium form. When a commercially available zeolite is used which has the required specifications concerning the Si/Al ratio, at least one ion exchange step is generally carried out in at least one $NH_4NO_3$ solution to obtain a zeolite with a sodium content of less than 0.1%, preferably less then 0.05% by weight, and in its $NH_4^+$ form.

It is also possible to start from a mordenite with a molar Si/Al ratio which is lower and generally in the range 5 to the desired value. Thus at least one dealumination step will be required to reach the desired Si/Al molar ratio. Within this context, any dealumination technique known to the skilled person can be used.

Using the operating method described in U.S. Pat. No. 4,780,436 in particular, calcining is carried out in a stream of dry air, then at least one ion exchange step using at least one $NH_4NO_3$ solution is carried out, to eliminate practically all of the alkaline cations, in particular sodium, present in the cationic position in the zeolite, then at least one framework dealumination cycle, steaming followed by an acid attack step, is carried out, comprising at least one calcining step carried out in the presence of steam, at a temperature which is generally in the range 550° C. to 850° C., followed by at least one acid attack step. The framework dealumination cycle, comprising at least one calcining step carried out on the mordenite in steam and at least one attack step carried out in an acid medium, can be repeated as many times as is necessary to obtain the desired characteristics. Similarly, after a calcining treatment carried out in steam, a number of successive acid attack steps, using different concentrations of acid solutions, can be carried out.

The mordenite can also be dealuminated by direct acid attack using all of the mineral or organic acids which are known to the skilled person. In the same manner as above, several acid attack steps may be necessary to achieve the desired Si/Al molar ratio. Mineral agents such as silica tetrachloride or ammonium hexafluorosilicate or organic agents such as the disodium salt of ethylenediaminetetraacetic acid can also produce the desired dealumination. Finally, this step can be carried out using dibasic carboxylic acids such as oxalic acid. Preferably, direct acid attack is carried out in a single step.

The zeolite which is at least partially in its acid form, with the high Si/Al molar ratio desired, must contain less than 0.1% by weight, preferably less than 0.05% by weight, of sodium.

The binder (or matrix) comprised in the catalyst of the present invention is generally selected from elements of the group formed by clays, magnesia, aluminas, silicas, titanium oxide, boron oxide, zirconia, aluminium phosphates, titanium phosphates, zirconium phosphates and silica aluminas. Preferably, the binder is alumina.

The catalyst can be prepared using any method which is known to the skilled person. In general, a mixture of the matrix and the zeolite is formed, followed by forming. Forming is generally followed by calcining, generally at a temperature in the range 250° C. to 600° C.

One preferred method for preparing the catalyst of the invention consists of mixing the zeolite in a moist gel of binder (generally obtained by mixing at least one acid and a powdered binder), for example alumina, for the period necessary to obtain good homogeneity of the paste produced, namely for about ten minutes, for example, then passing the paste through a die to form extrudates, for example with a diameter in the range 0.4 mm to 4 mm. The extruded paste is oven dried for several minutes at 100° C. then calcined, for example for two hours at 400° C.

The catalyst of the invention is generally formed so that the catalyst is preferably obtained for subsequent use in the form of pellets, aggregates, extrudates or spherules.

Preparation of the catalyst generally ends with final calcining, normally at a temperature which is in the range 250° C. to 600° C., preferably preceded by drying, for example oven drying, at a temperature which is in the range from ambient temperature to 250° C., preferably 40° C. to 200° C. The drying step is preferably carried out during the temperature rise required to carry out calcining.

The catalyst of the present invention is used in a process for dismutation of toluene to produce benzene and xylenes, and/or transalkylation of alkylaromatics, preferably toluene with AC9(+) to produce xylenes, from toluene-AC9(+) mixtures generally containing at most 50 mole % of AC9(+). The process is generally carried out using the following operating conditions: a temperature in the range 250° C. to 600° C., preferably in the range 330° C. to 500° C.; a pressure in the range 10 to 60, preferably in the range 20 to 45 bar (1 bar=0.1 MPa); an hourly space velocity expressed in kilograms of feed introduced per kilogram of catalyst per hour, in the range 0.1 to 10, preferably in the range 0.5 to 4; and a molar ratio of hydrogen to hydrocarbon(s) in the range 2 to 20, preferably in the range 3 to 12.

The following examples illustrate the invention without limiting its scope.

EXAMPLE 1

Preparation of Catalyst C1, Not in Accordance with the Invention

The starting zeolite was a mordenite in its sodium form, with an Si/Al ratio of 20.2 and a unit cell volume of 2.737 nm$^3$. The zeolite underwent ion exchange in a 10 N NH$_4$NO$_3$ solution at about 100° C. for 4 hours. The solid obtained contained 25 ppm of sodium.

This zeolite in its hydrogen form was then formed by extrusion with an alumina gel to obtain, after drying and calcining in dry air, a catalyst C1 which contained 80% by weight of mordenite zeolite in its H form and 20% of alumina.

EXAMPLE 2

Preparation of Catalyst C2, in Accordance with the Invention

The starting material used was a mordenite zeolite, which had a global Si/Al atomic ratio of 7.6, and a sodium content, with respect to the weight of dry mordenite zeolite, of about 3.8% by weight.

This mordenite zeolite underwent acid attack, using an 8 N nitric acid solution at about 100° C. for 4 hours, to partially extract the aluminium atoms present in the zeolitic framework of the mordenite. The dealuminated mordenite zeolite then underwent ion exchange in a 10 N NH$_4$NO$_3$ solution at about 100° C. for 4 hours to extract the residual sodium.

After these treatments, the mordenite zeolite in its H form had a global Si/Al atomic ratio of 47.9, and a sodium content, with respect to the weight of dry mordenite zeolite, of 48 ppm by weight.

This zeolite was then formed by extrusion with an alumina gel to obtain, after drying and calcining in dry air, a catalyst C2 which contained 80% by weight of mordenite zeolite in its H form and 20% of alumina.

EXAMPLE 3

Evaluation of Catalytic Properties of Catalysts C1 (Not in Accordance) and C2 (in Accordance)

The performances of catalysts C1 and C2 were evaluated for transformation of toluene to produce benzene and xylenes. The operating conditions were as follows:

temperature: 450° C.;

pressure: 30 bar (1 bar=0.1 MPa);

hydrogen/toluene molar ratio: 5.

The conversions, xylene yields and benzene+xylene selectivities are shown in Table 1 below.

TABLE 1

| Catalyst | Conversion (weight %) | Xylene yield weight (%) | Benzene + xylenes selectivity (weight %) |
|---|---|---|---|
| C1 (not in accordance) | 49.1 | 22.5 | 88.9 |
| C2 (in accordance) | 50.6 | 22.8 | 89.5 |

It can be seen that catalyst C2 of the invention was more active that catalyst C1 which was not in accordance with the invention, and, further, catalyst C2 led to an improved xylene yield and benzene+xylenes selectivity over catalyst C1.

Further, the stability of catalysts C1 and C2 was evaluated by measuring the toluene conversion after injecting the feed for 14 days. The conversions after 5 days and 14 days of operation are indicated in Table 2 below.

TABLE 2

| Toluene conversion (weight %) | Catalyst C1 (comparative) | Catalyst C2 (in accordance with invention) |
|---|---|---|
| 5 days operation | 50.2 | 51.1 |
| 14 days operation | 45.4 | 48.8 |
| Percentage deactivation | 9.6 | 4.5 |

The percentage deactivation represents the difference between the conversion at 14 days of operation and that at 5 days of operation, with respect to conversion at 5 days of operation.

It can be seen that the deactivation of catalyst C2 of the invention was only 4.5% while that of catalyst C1 was 9.6% over the same period. Catalyst C2 of the invention thus has a substantially improved stability over time compared with comparative catalyst C1.

We claim:

1. A final calcined catalyst for dismutation and/or transalkylation of toluene and/or alkylaromatic compounds containing at least 9 carbon atoms per molecule consisting essentially of:

40% to 90% by weight of at least one zeolite with a mordenite structure which is at least partially in its acid form, having a Si/Al molar ratio in the range of 40 to 60, said mordenite containing at most 0.1% by weight (expressed with respect to zeolite) of sodium;

10% to 60% by weight of at least one binder.

2. A catalyst according to claim 1, comprising 75% to 85% by weight of zeolite and 15% to 25% by weight of binder.

3. A catalyst according to claim 1, in which the binder is selected from the group consisting of clays, magnesia, aluminas, silicas, titanium oxide, boron oxide, zirconia, aluminium phosphates, titanium phosphates, zirconium phosphates and silica aluminas.

4. A catalyst according to claim 1, in which the binder is an alumina.

5. In a process for the dismutation and/or transalkylation of a compound selected from the group consisting of toluene and alkylaromatics containing at least 9 carbon atoms per molecule, the improvement comprising contacting said compounds with the catalyst of claim 1.

6. The process according to claim 5 wherein benzene and xylene are produced by the dismutation of toluene.

7. The process according to claim 5 wherein xylenes are produced by the transalkylation of toluene with alkylaromatics containing at least 9 carbon atoms per molecule and wherein the reaction mixture contains at most 50 mole % of said alkylaromatics.

8. The process according to claim 5, wherein the catalyst comprises 75% to 85% by weight of zeolite and 15% to 25% by weight of binder.

9. The process according to claim 5, wherein the binder is alumina.

10. A process according to claim 5, carried out under the following operating conditions: a temperature in the range 250° C. to 600° C.; a pressure in the range 1 to 6 MPa; an hourly space velocity, expressed in kilograms of feed introduced per kilogram of catalyst per hour, in the range 0.1 to 10; and a hydrogen to total hydrocarbon molar ratio which is in the range 2 to 20.

* * * * *